United States Patent [19]

Bastard et al.

[11] Patent Number: 5,403,858
[45] Date of Patent: Apr. 4, 1995

[54] NEW COMPOSITIONS CONTAINING TAXANE DERIVATIVES

[75] Inventors: Jean-Pierre Bastard, Lesigny; Thierry Dupechez, Villemoisson sur Orge; Jean-Louis Fabre, Paris, all of France

[73] Assignee: Rhone-Poulenc Rorer, S.A., Antony, France

[21] Appl. No.: 930,392

[22] PCT Filed: Jul. 3, 1992

[86] PCT No.: PCT/FR92/00624

§ 371 Date: Aug. 23, 1993

§ 102(e) Date: Aug. 23, 1993

[87] PCT Pub. No.: WO93/00928

PCT Pub. Date: Jan. 21, 1993

[30] Foreign Application Priority Data

Jul. 8, 1991 [FR] France .................. 91 08527

[51] Int. Cl.⁶ .................. A61K 31/335; A61K 31/34; A61K 9/50

[52] U.S. Cl. .................. 514/449; 514/471; 514/408; 424/502

[58] Field of Search .................. 514/471, 408, 449; 424/502

[56] References Cited

U.S. PATENT DOCUMENTS

4,206,221  6/1980  Miller et al. .................. 514/471
4,960,790 10/1990  Stella et al. .................. 514/449

OTHER PUBLICATIONS

Chemical Abstracts: vol. 106(22) 182581c–Tarr, et al (1987).
Merck Index, 11th Edition, #7559—(1989).

*Primary Examiner*—Raymond Henley, III
*Assistant Examiner*—T. J. Criares
*Attorney, Agent, or Firm*—Morgan & Finnegan

[57] ABSTRACT

Compositions containing taxane derivatives, consist of a solution of such derivative in a surfactant consisting of polysorbate, polyethelene glycol or hydrogenated castor oil. These compositions can be used to prepare perfusion solutions essentially free of ethanol.

17 Claims, No Drawings

NEW COMPOSITIONS CONTAINING TAXANE DERIVATIVES

The present invention relates to compositions and especially pharmaceutical dosage forms containing therapeutic agents having antitumour and antileukaemic activity. It relates more especially to compositions suitable for injection containing taxane derivatives, such as, in particular, taxol or one of its analogues or derivatives of the formula:

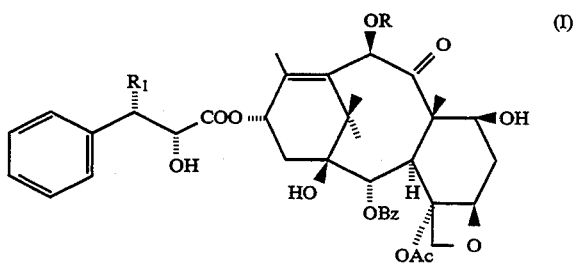

in which R represents a hydrogen atom or an acetyl radical and $R_1$ represents a tert-butoxycarbonylamino or benzoyloxyamino radical. Of these derivatives, that in which R represents an acetyl group and $R_1$ represents a benzoyloxyamino group or that in which R represents a hydrogen atom and $R_1$ represents a tert-butoxycarbonylamino radical are preferred. The first of these two compounds is better known by the name of taxol, and the second is known by the name of Taxotere.

These products exhibit in vivo substantial activity against malignant rumours, which has enabled them to be studied in the treatment of diseases resistant to other anticancer therapies.

Unfortunately, these products possess such low solubility in water that it has been necessary to prepare formulations for injection containing surfactant and ethanol. Ethanol is the best solvent for dissolving compounds of formula (I).

For example, according to the publication by Rowinsky, Lorraine, Cazenave and Donehower which appeared in the Journal of the National Cancer Institute, vol. 82, No. 15, pages 1247–1259 on 1st Aug. 1990, a first solution, termed "stock solution", containing approximately 6 mg/ml of taxol in a solvent mixture composed of:

50% by volume of ethanol
50% by volume of Cremophor EL, is prepared. On injection, this solution is mixed with a perfusion fluid containing sodium chloride or dextrose (glucose). To obtain a mixture which is stable from both a physical standpoint and a chemical standpoint, the authors of this paper state that it is necessary to limit the concentration of active principle in the perfusion solution to concentrations of approximately 0.03 to 0.6 mg/ml (see above publication, page 1251, column 1, third paragraph).

Now, it is desirable to be able to inject sufficient doses of active principle; to this end, clinicians would like to inject concentrations of active principle of between approximately 0.3 and 1 mg/ml in the perfusion fluid; above these doses, anaphylactic shock phenomena which are difficult to control, due in the main to the Cremophor, are seen (see the publication by Rowinsky, page 1250, second column, last paragraph).

Still according to this publication, to obtain such concentrations (between 0.3 and 1 mg/ml), it is necessary to inject solutions containing, at the same time as the active principle, concentrations of each of the following compounds, ethanol and most especially Cremophor, of approximately 8 g per 100 ml of solution. Since the treatment often requires the administration of high doses of active principle, and since the concentration of the active principle in the solution is relatively low, the injection of a large volume has the effect of causing, in addition to anaphylactic manifestations, manifestations of alcohol poisoning during the treatment.

The present invention provides compositions that make it possible either to reduce the ethanol concentrations greatly, or to eliminate Cremophor and ethanol completely from the perfusions.

For this purpose, according to a first implementation of the present invention, a composition suitable for use as a stock solution is prepared, containing a compound of formula I as defined above dissolved in a surfactant which may be a polysorbate, e.g. as marketed under the name "Tween", a polyoxyethylene glycol ester as marketed, e.g., under the name "Emulphor", or an ester of polyethylene glycol and castor oil as marketed, e.g., under the name Cremophor, and virtually free from ethanol.

The stock solution may be prepared by dissolving the active principle in ethanol, which is the best biocompatible solvent for the taxane derivatives, and then gradually adding the surfactant. Solutions containing 10 to 100 mg/ml of active principle in a mixture containing approximately 50% of surfactant can be prepared in this manner. The ethanol is then completely, or almost completely, eliminated.

To prepare, according to the present invention, the solution having a low ethanol content, the taxane derivative is dissolved in ethanol, and the surfactant, which enables micelles to be formed containing the taxane derivative encapsulated in the surfactant after dilution in an aqueous medium, is then added. The ethanol contained in this solution is then removed at least partially by evaporation under vacuum or by any other suitable means.

According to a second method for preparing the stock solution, the taxane derivative is dissolved directly in the surfactant. According to a preferred method, a solution of surfactant containing, in particular, 1 to 2% of ethanol is prepared, and the taxane derivative is added continuously to this solution with stirring, e.g. using a helical grinder or a centrifugal disintegrator. The presence of a small amount of ethanol provides several advantages: the medium possesses a lower viscosity, and the wetting of the powder and the final filtration of the solution are improved.

The stock solution, having a low ethanol content, preferably contains less than 5% of ethanol; still more preferably, it contains less than 2% of ethanol. This solution is stable and can contain up to 200 mg/ml, preferably up to 80 mg/ml, of active principle in the surfactant.

A stock solution of taxol possesses still more preferably a concentration of between 6 and 20 mg/ml of active principle in the surfactant. This solution can be mixed, in particular to provide a final concentration of between 0.1 and 1 mg per milliliter, with the perfusion fluid, which can be physiological saline or a glucose solution. Perfusions prepared from the above stock solutions having a low ethanol content contain still more preferably between 0.3 and 0.5 mg/ml of taxol and less than 1 ml/l of ethanol.

The taxol perfusion containing the active principle without ethanol possesses a physical stability of between 8 and about one hundred hours. Physical stability is understood to wean that the solution does not exhibit any visible precipitation after 8 to 10 hours of storage at room temperature.

A stock solution of Taxotere preferably possesses a concentration of between 20 and 80 mg/ml of active principle in the surfactant. This solution can be mixed, in particular to provide a final concentration of between 0.1 and 0.5 mg per milliliter, with the perfusion fluid, which can be a physiological saline or a glucose solution. Perfusions prepared from the above stock solutions having a low ethanol content contain still more preferably between 0.1 and 0.3 mg/ml of Taxotere; they preferably contain less than 15 ml/l of surfactant and less than 1 ml/l of ethanol.

The Taxotere perfusion containing the active principle without ethanol possesses a physical stability which can reach several months.

The taxol or Taxotere perfusions may be injected into humans at a predetermined flow rate depending on the amount of active principle it is desired to inject. The anaphylactic shock phenomena which were observed with the solutions of the prior can be avoided with these solutions.

Thus, these perfusions have made it possible to reduce, relative to the prior art, the amount of surfactant injected into humans by approximately 80% and the amount of ethanol by almost 100%.

The invention is illustrated by the following Examples.

COMPARATIVE EXAMPLE ACCORDING TO THE PRIOR ART

Taxol (0.180 g) is dissolved in ethanol (15 ml). The mixture is made to volume with Cremophor to obtain a solution (30 ml) which contains taxol (6 mg/ml).

This solution is diluted in a 5% glucose perfusion solution in a proportion of 1 mg/ml; the perfusion solution contains 87.7 ml/l of Cremophor and 87.7 ml/l of ethanol. The perfusion solution is stable for more than 21 hours.

EXAMPLES 1-7

Taxotere (32 g) is dissolved in absolute ethanol (340 ml) and Polysorbate 80 (830 g) is then added. The ethanol is evaporated off in a rotary evaporator at 30° C. at a pressure of 15 mmHg for 2 hours. The solution obtained is stable; it contains Taxotere (40 mg/ml).

After dilution in a 5% glucose perfusion solution at concentrations of 0.1, 0.3 and 0.5 mg/ml, the stability of the solutions obtained is observed.

The same method is reproduced using a solution containing Taxotere (60 mg/ml).

The same test is reproduced using taxol solutions containing taxol (12 and 20 mg/ml).

The results are shown in Table 1.

TABLE 1

| Product | Solvent | Stock solution concentration | Active principle in the perfusion | Surfactant in the perfusion | Ethanol in the perfusion | Stability |
| --- | --- | --- | --- | --- | --- | --- |
| taxol | Polysorbate | 20 mg/ml | 1 mg/ml | 50 ml/l | <0.3 ml/l | >8 H |
| taxol | Polysorbate | 20 mg/ml | 0.3 mg/ml | 15 ml/l | <0.09 ml/l | >24 H |
| taxol | Polysorbate | 12 mg/ml | 1 mg/ml | 83.3 ml/l | <0.5 ml/l | >48 H |
| Taxotere | Polysorbate | 40 mg/ml | 0.5 mg/ml | 11.6 ml/l | 0.09 ml/l | 8 H–23 H |
| Taxotere | Polysorbate | 40 mg/ml | 0.3 mg/ml | 6.9 ml/l | 0.05 ml/l | 8 H–23 H |
| Taxotere | Polysorbate | 40 mg/ml | 0.1 mg/ml | 2.3 ml/l | 0.02 ml/l | 29 H–45 H |
| Taxotere | Polysorbate | 60 mg/ml | 0.1 mg/ml | 1.5 ml/l | <0.01 ml/l | 8 H–23 H |

EXAMPLE 8

Into a stainless steel reactor, Taxotere (258 g) is introduced and dissolved in ethanol (2425 g) with mechanical stirring for 45 minutes. Polysorbate 80 (6156 g) is added and the mixture is homogenised with mechanical stirring for 15 minutes. The solution is transferred to a reactor and the alcohol is distilled off under a reduced pressure of 10 to 50 millibars (1000 to 5000 Pa), the temperature being maintained at between 18° and 28° C. The alcohol is distilled off until its content is less than 2%.

The solution obtained is filtered through a filter having a pore size of 0.2 μm. It contains:
ethanol ( 1.3% )
Taxotere (39.6 mg/ml).

After dilution to 1 mg/ml in a perfusion bag containing 5% glucose, the solution is stable without apparent precipitation for a period of more than 2 months.

EXAMPLE 9

Taxotere (160 mg) or taxol (160 mg) is dissolved in a mixture (10 ml) of absolute ethanol (2 ml) and Cremophor EL(218) (8 ml), and the ethanol is evaporated off in a rotary evaporator at 30° C. at a pressure of 25 mmhg for 3 hours. The solutions obtained are stable. They contain 20 mg/ml of Taxotere or taxol. After dilution in a 5% glucose perfusion solution at concentrations of 0.1 and 0.5 mg/ml, precipitation is observed at between 30 and 95 hours.

EXAMPLE 10

Polysorbate 80 (275.5 g) and absolute ethanol (5.4 g) are placed in a 500-ml Erlenmeyer flask, and the mixture is then stirred with a bar magnet until completely homogenised.

The solution prepared above (26.13 g) in a 50 ml flask, placed in a water bath heated beforehand and maintained throughout the test period at 30° C., is stirred at approximately 600 rpm with a bar magnet. With a spatula, Taxotere (1.076 g) is added in several portions so that the clumps disappear between two additions (the duration of the operation is approximately one hour). After incorporation of the last fraction of Taxotere, stirring is maintained until the solution becomes clear (approximately two hours).

We claim:

1. A composition consisting essentially of a compound of formula:

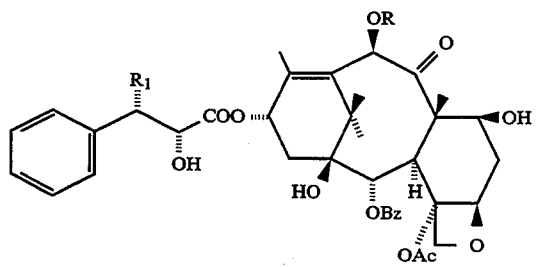

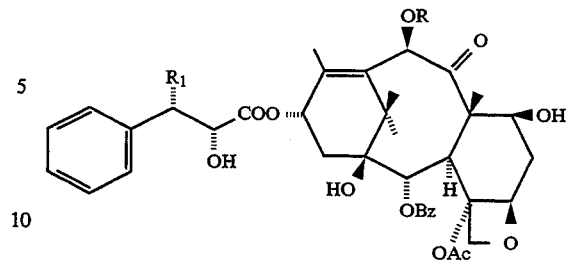

in which R represents a hydrogen atom or an acetyl radical and $R_1$ represents a tert-butoxycarbonylamino or benzoylamino radical, dissolved in a surfactant selected from the group consisting of polysorbate, polyoxyethylene glycol and hydrogenated castor oil, and essentially free of ethanol.

2. A composition according to claim 1, which contains less than 5% by volume of ethanol.

3. A composition according to claim 1, wherein, in the compound of formula (I), R represents hydrogen and $R_1$ represents a tert-butoxycarbonylamino radical.

4. A composition according to claim 1, wherein, in the compound of formula (I), R represents an acetyl group and $R_1$ represents a benzoyloxyamino radical.

5. A composition according to claim 1, which contains up to 200 mg/ml of compound of formula (I).

6. A composition according to claim 3, which contains 20 to 80 mg/ml of compound of formula (I).

7. A composition according to claim 4, which contains 6 to 20 mg/ml of compound of formula (I).

8. A composition according to claim 2, wherein the composition contains less than 2% of ethanol.

9. A composition according to claim 5, which contains up to 80 mg/ml of compound of formula (I).

10. Composition consisting essentially of a taxane derivative of the formula:

in which R represents a hydrogen atom or an acetyl radical and $R_1$ represents a tert-butoxycarbonylamino or benzoylamino radical dissolved in a surfactant selected from the group consisting of polysorbate, polyoxyethylene glycol and hydrogenated castor oil, said composition containing less than 5% by volume ethanol.

11. Composition according to claim 10, wherein ethanol is less than 2% by volume.

12. A perfusion comprising less than 0.5 mg/ml of compound as defined in claim 3 and less than 1 ml/l of ethanol and less than 15 ml/l of surfactant.

13. A perfusion, comprising 1 mg/ml or less of compound as defined in claim 4 and less than 1 ml/l of ethanol.

14. A perfusion according to claim 12, wherein the perfusion contains 0.1 to 0.3 mg/ml of a compound of formula (I) wherein R represents hydrogen and $R_1$ represents a tert-butoxycarbonylamino radical.

15. A method for preparing a composition according to claim 1, which comprises dissolving a compound of formula (I) in ethanol, adding the surfactant and removing the ethanol.

16. A method for preparing a composition according to claim 1, which comprises slowly adding a compound of formula (I) to a solution of the surfactant containing 1 to 2% by volume of ethanol.

17. A method for preparing a composition according to claim 15, wherein ethanol is removed by evaporation.

* * * * *